(12) United States Patent
Rusanen et al.

(10) Patent No.: US 12,064,647 B2
(45) Date of Patent: Aug. 20, 2024

(54) METHOD AND APPARATUS TO FACILITATE GENERATING A LEAF SEQUENCE FOR A MULTI-LEAF COLLIMATOR

(71) Applicant: Siemens Healthineers International AG, Steinhausen (CH)

(72) Inventors: Marko T. Rusanen, Espoo (FI);
Jarkko Y. Peltola, Tuusula (FI);
Shahab Basiri, Helsinki (FI); Esa Kuusela, Espoo (FI)

(73) Assignee: Siemens Healthineers International AG, Steinhausen (CH)

( * ) Notice: Subject to any disclaimer, the term of this patent is extended or adjusted under 35 U.S.C. 154(b) by 566 days.

(21) Appl. No.: 17/361,817

(22) Filed: Jun. 29, 2021

(65) Prior Publication Data
US 2022/0409929 A1 Dec. 29, 2022

(51) Int. Cl.
| | |
|---|---|
| *A61N 5/10* | (2006.01) |
| *G05B 13/02* | (2006.01) |
| *G06N 3/09* | (2023.01) |
| *G06N 3/092* | (2023.01) |
| *G16H 20/40* | (2018.01) |
| *G16H 40/63* | (2018.01) |
| *G16H 50/20* | (2018.01) |
| *G16H 50/70* | (2018.01) |

(52) U.S. Cl.
CPC ......... *A61N 5/1036* (2013.01); *A61N 5/1031* (2013.01); *A61N 5/1045* (2013.01); *G05B 13/027* (2013.01); *G06N 3/09* (2023.01); *G06N 3/092* (2023.01); *G16H 20/40* (2018.01); *G16H 40/63* (2018.01); *G16H 50/20* (2018.01); *G16H 50/70* (2018.01)

(58) Field of Classification Search
CPC .. A61N 5/1031; A61N 5/1036; A61N 5/1045; G05B 13/027; G06N 3/09; G06N 3/092; G16H 20/40; G16H 40/63; G16H 50/20; G16H 50/70
See application file for complete search history.

(56) References Cited

U.S. PATENT DOCUMENTS

| | | | |
|---|---|---|---|
| 7,831,018 B1 * | 11/2010 | Nord | A61N 5/1045 378/65 |
| 2018/0272152 A1 * | 9/2018 | Kuusela | A61N 5/1031 |

(Continued)

FOREIGN PATENT DOCUMENTS

WO WO-2019113234 A1 * 6/2019 ............. A61N 5/103

OTHER PUBLICATIONS

PCT Search Report and Written Opinion from related International Application No. PCT/EP2022/067509 dated Sep. 19, 2022; 15 pages.

*Primary Examiner* — Mark R Gaworecki
(74) *Attorney, Agent, or Firm* — Fitch, Even, Tabin & Flannery LLP

(57) ABSTRACT

A memory has a fluence map that corresponds to a particular patient stored therein. This memory also has at least one deep learning model stored therein trained to deduce a leaf sequence for a multi-leaf collimator from a fluence map. A control circuit operably coupled to that memory iteratively optimizes a radiation treatment plan to administer therapeutic radiation to that patient by, at least in part, generating a leaf sequence as a function of the at least one deep learning model and the fluence map that corresponds to the patient.

16 Claims, 4 Drawing Sheets

(56) References Cited

U.S. PATENT DOCUMENTS

| | | |
|---|---|---|
| 2019/0076671 A1 | 3/2019 | Willcut |
| 2019/0175952 A1 | 6/2019 | Hissoiny |
| 2019/0209864 A1 | 7/2019 | Stahl |
| 2020/0069969 A1 | 3/2020 | Heese |
| 2022/0088410 A1* | 3/2022 | Hibbard ................. G16H 20/40 |

* cited by examiner

METHOD AND APPARATUS TO FACILITATE GENERATING A LEAF SEQUENCE FOR A MULTI-LEAF COLLIMATOR

TECHNICAL FIELD

These teachings relate generally to treating a patient's planning target volume with radiation pursuant to a radiation treatment plan and more particularly to generating a radiation treatment plan for that patient.

BACKGROUND

The use of radiation to treat medical conditions comprises a known area of prior art endeavor. For example, radiation therapy comprises an important component of many treatment plans for reducing or eliminating unwanted tumors. Unfortunately, applied radiation does not inherently discriminate between unwanted materials and adjacent tissues, organs, or the like that are desired or even critical to continued survival of the patient. As a result, radiation is ordinarily applied in a carefully administered manner to at least attempt to restrict the radiation to a given target volume. A so-called radiation treatment plan often serves in the foregoing regards.

A radiation treatment plan typically comprises specified values for each of a variety of treatment-platform parameters during each of a plurality of sequential fields. Treatment plans for radiation treatment sessions are often generated through a so-called optimization process. As used herein, "optimization" will be understood to refer to improving a candidate treatment plan without necessarily ensuring that the optimized result is, in fact, the singular best solution. Such optimization often includes automatically adjusting one or more treatment parameters (often while observing one or more corresponding limits in these regards) and mathematically calculating a likely corresponding treatment result to identify a given set of treatment parameters that represent a good compromise between the desired therapeutic result and avoidance of undesired collateral effects.

Multi-leaf collimators are known in the art and are often employed when administering therapeutic radiation to a patient. Multi-leaf collimators are comprised of a plurality of individual parts (known as "leaves") that are formed of a high atomic numbered material (such as tungsten) that can move independently in and out of the path of the radiation-therapy beam in order to selectively block (and hence shape) the beam. Typically the leaves of a multi-leaf collimator are organized in pairs that are aligned collinearly with respect to one another and which can selectively move towards and away from one another. A typical multi-leaf collimator has many such pairs of leaves, often upwards of twenty, fifty, or even one hundred such pairs.

When optimizing a radiation treatment plan with respect to a multi-leaf collimator, the optimization process itself may seek an optimal position for each pair of leaves independent of all other leaf pairs (for each field of exposure at a given control point) by iteratively testing a variety of such positions. This optimization may further include optimizing a particular sequence of leaf movements from one control point to another. That sequence optimization may occur during the above-described optimization iterations (as typically occurs when formulating VMAT plans). Unfortunately such sequence optimizing can be relatively unduly time-consuming and/or rely upon faster leaf-sequencing algorithms that are relatively complex and difficult to adjust on a case-by-case basis. Such computations may be further encumbered by a need to accommodate various physical restrictions and speed limits that may need to be taken into account as regards the leaves themselves.

BRIEF DESCRIPTION OF THE DRAWINGS

The above needs are at least partially met through provision of the method and apparatus to facilitate generating a leaf sequence or a multi-leaf collimator described in the following detailed description, particularly when studied in conjunction with the drawings, wherein.

Figure 1:
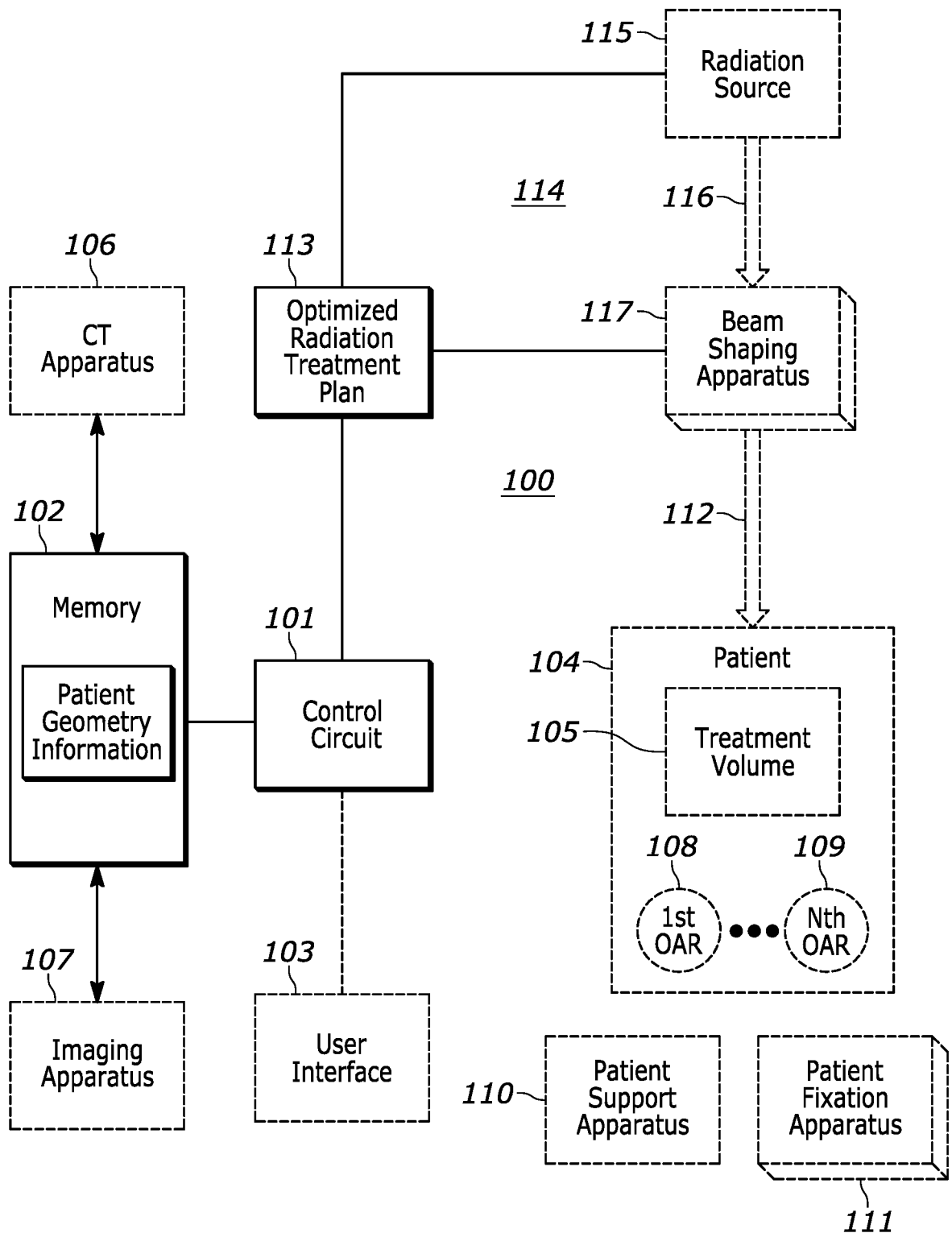
FIG. 1 comprises a block diagram as configured in accordance with various embodiments of these teachings.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present teachings. Also, common but well-understood elements that are useful or necessary in a commercially feasible embodiment are often not depicted in order to facilitate a less obstructed view of these various embodiments of the present teachings. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein. The word "or" when used herein shall be interpreted as having a disjunctive construction rather than a conjunctive construction unless otherwise specifically indicated.

DETAILED DESCRIPTION

Generally speaking, these various embodiments support the development of an optimized radiation treatment plan to effect radiation-based treatment of a patient's planning treatment volume. For the sake of an illustrative example these teachings can be carried out at least in part by an enabling control circuit. That control circuit may, or may not, be part of an integrated circuit.

These teachings provide a memory having a fluence map that corresponds to a particular patient stored therein. This memory also has at least one deep learning model stored therein trained to deduce a leaf sequence for a multi-leaf collimator from a fluence map. By one approach, a control circuit operably coupled to that memory and is configured to iteratively optimize a radiation treatment plan to administer therapeutic radiation to that patient by, at least in part, generating a leaf sequence as a function of the at least one deep learning model and the fluence map that corresponds to the patient.

By one approach the memory has a plurality of such deep learning models stored therein. In this case the control circuit may be further configured to select at least a particular one of the deep learning models for use in generating the leaf sequence.

By one approach at least one of the plurality of deep learning models outputs relatively higher monitor unit solutions. By another approach, in lieu of the foregoing or in combination therewith, at least one of the plurality of deep learning models outputs relatively lower monitor unit solutions.

These teachings are flexible in practice and will accommodate various approaches depending upon the particular application setting. By one approach, the aforementioned deep learning model comprises a neural network model. In such a case, that neural network model may be trained, at least in part, via a supervised learning method. As another example, the neural network model may be trained using a training corpus that includes fluence maps for each of a plurality of corresponding field/control points. As yet another example, the neural network model may be trained, at least in part, via a reinforcement learning method.

So configured, the deep learning model facilitates deducing a leaf sequence from the fluence map for a given patient. As the inference step for artificial intelligence models is typically relatively fast (especially as compared to prior art practice), these teachings can greatly speed up the leaf sequencing part of a radiation treatment plan optimization process while also making the planning more adjustable in view of specific considerations corresponding to a given use case (for example, by using multiple models). Such a savings in time can yield numerous benefits. For example, a given planning platform (and possibly its associated treatment platform) can be more productive and serve more patients than prior art practitioners would typically expect in a given time window. As another example, in some cases these teachings will reduce the amount of time a patient may need to lie in waiting in/on the treatment platform while the planning process transpires.

These and other benefits may become clearer upon making a thorough review and study of the following detailed description. Referring now to the drawings, and in particular to FIG. 1, an illustrative apparatus 100 that is compatible with many of these teachings will now be presented.

In this particular example, the enabling apparatus 100 includes a control circuit 101. Being a "circuit," the control circuit 101 therefore comprises structure that includes at least one (and typically many) electrically-conductive paths (such as paths comprised of a conductive metal such as copper or silver) that convey electricity in an ordered manner, which path(s) will also typically include corresponding electrical components (both passive (such as resistors and capacitors) and active (such as any of a variety of semiconductor-based devices) as appropriate) to permit the circuit to effect the control aspect of these teachings.

Such a control circuit 101 can comprise a fixed-purpose hard-wired hardware platform (including but not limited to an application-specific integrated circuit (ASIC) (which is an integrated circuit that is customized by design for a particular use, rather than intended for general-purpose use), a field-programmable gate array (FPGA), and the like) or can comprise a partially or wholly-programmable hardware platform (including but not limited to microcontrollers, microprocessors, and the like). These architectural options for such structures are well known and understood in the art and require no further description here. This control circuit 101 is configured (for example, by using corresponding programming as will be well understood by those skilled in the art) to carry out one or more of the steps, actions, and/or functions described herein.

The control circuit 101 operably couples to a memory 102. This memory 102 may be integral to the control circuit 101 (as when the memory 102 and control circuit 101 are both included on a shared integrated circuit) or can be physically discrete (in whole or in part) from the control circuit 101 as desired. This memory 102 can also be local with respect to the control circuit 101 (where, for example, both share a common circuit board, chassis, power supply, and/or housing) or can be partially or wholly remote with respect to the control circuit 101 (where, for example, the memory 102 is physically located in another facility, metropolitan area, or even country as compared to the control circuit 101).

In addition to optimization objectives information, patient geometry information, field geometry information, and so forth this memory 102 can serve, for example, to non-transitorily store the computer instructions that, when executed by the control circuit 101, cause the control circuit 101 to behave as described herein. (As used herein, this reference to "non-transitorily" will be understood to refer to a non-ephemeral state for the stored contents (and hence excludes when the stored contents merely constitute signals or waves) rather than volatility of the storage media itself and hence includes both non-volatile memory (such as read-only memory (ROM) as well as volatile memory (such as a dynamic random access memory (DRAM).)

By one optional approach the control circuit 101 also operably couples to a user interface 103. This user interface 103 can comprise any of a variety of user-input mechanisms (such as, but not limited to, keyboards and keypads, cursor-control devices, touch-sensitive displays, speech-recognition interfaces, gesture-recognition interfaces, and so forth) and/or user-output mechanisms (such as, but not limited to, visual displays, audio transducers, printers, and so forth) to facilitate receiving information and/or instructions from a user and/or providing information to a user.

In this illustrative example the control circuit 101 also operably couples to a network interface 118 that communicatively couples to one or more communication networks 119 (such as, but not limited to, the Internet). So configured the control circuit 101 can communicate with other elements (both within the apparatus 100 and external thereto, such as one or more remote entities 120) via the network interface 118. Network interfaces, including both wireless and non-wireless platforms, are well understood in the art and require no particular elaboration here.

By one approach, a computed tomography apparatus 106 and/or other non-CT imaging apparatus 107 as are known in the art can source some or all of any desired patient-related imaging information.

In this illustrative example the control circuit 101 is configured to also optionally output an optimized radiation treatment plan 113. This radiation treatment plan 113 typically comprises specified values for each of a variety of treatment-platform parameters during each of a plurality of sequential fields. In this case the radiation treatment plan 113 is generated through an optimization process. Various non-automated, automated, or partially-automated optimization processes specifically configured to generate such a radiation treatment plan are known in the art. As the present teachings are not overly sensitive to any particular selections in these regards, further elaboration in these regards is not provided here except where particularly relevant to the details of this description.

By one approach the control circuit 101 can operably couple to a radiation treatment platform 114 that is configured to deliver therapeutic radiation 112 to a corresponding patient 104 in accordance with the optimized radiation treatment plan 113. These teachings are generally applicable for use with any of a wide variety of radiation treatment platforms. In a typical application setting the radiation treatment platform 114 will include a radiation source 115. The radiation source 115 can comprise, for example, a radio-frequency (RF) linear particle accelerator-based (linac-based) x-ray source, such as the Varian Linatron M9. The linac is a type of particle accelerator that greatly increases the kinetic energy of charged subatomic particles or ions by subjecting the charged particles to a series of oscillating electric potentials along a linear beamline, which can be used to generate ionizing radiation (e.g., X-rays) 116 and high energy electrons.

A typical radiation treatment platform 114 may also include one or more support apparatuses 110 (such as a couch) to support the patient 104 during the treatment session, one or more patient fixation apparatuses 111, a gantry or other movable mechanism to permit selective movement of the radiation source 115, and one or more beam-shaping apparatuses 117 (such as jaws, multi-leaf collimators, and so forth) to provide selective beam shaping and/or beam modulation as desired. As the foregoing elements and systems are well understood in the art, further elaboration in these regards is not provided here except where otherwise relevant to the description.

Figure 2:
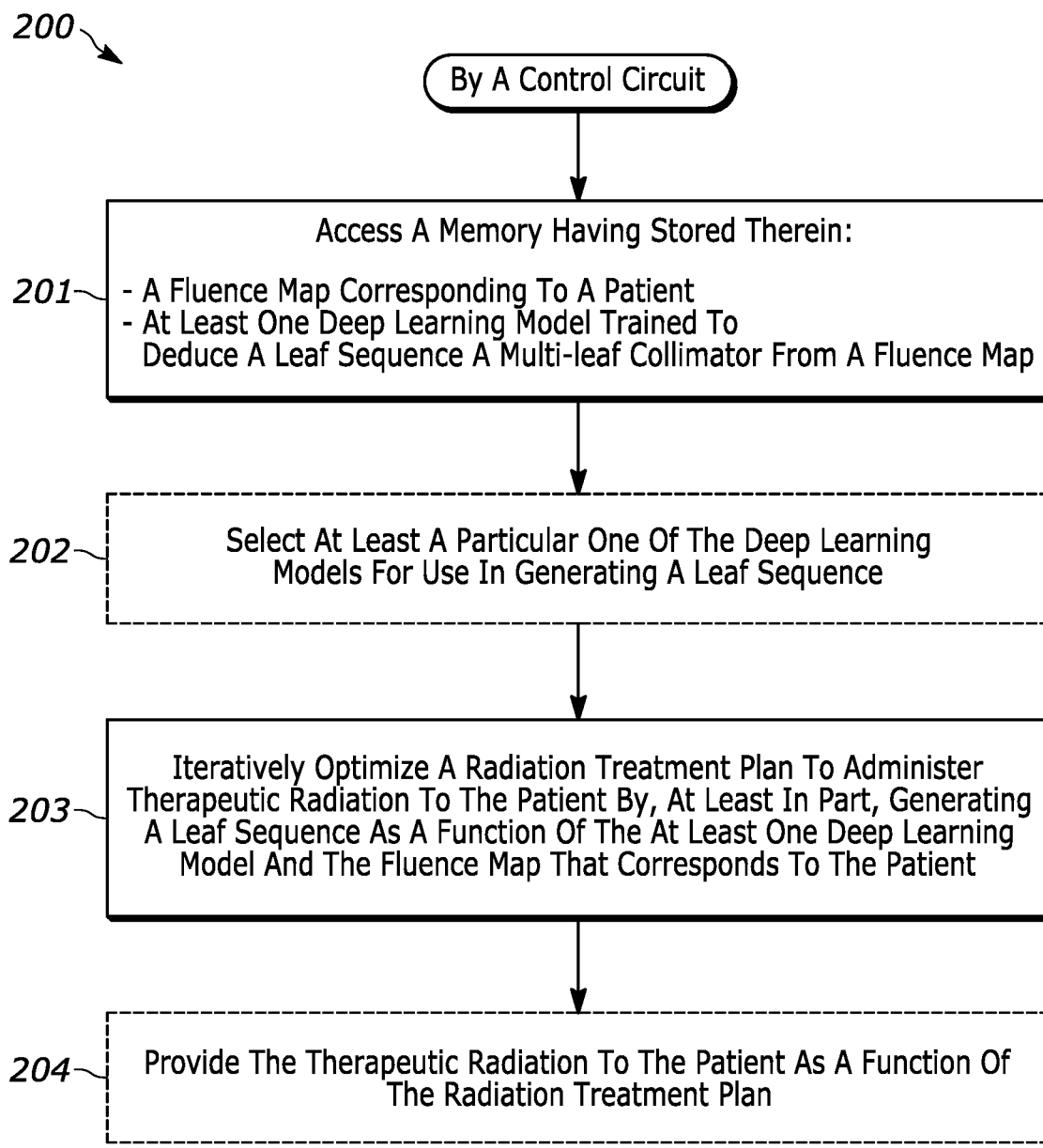
FIG. 2 comprises a flow diagram as configured in accordance with various embodiments of these teachings.

Referring now to FIG. 2, a process 200 that can be carried out, for example and at least in part, by the above-described control circuit 101 will be presented.

At block 201, this process 200 provides for accessing a memory such as the aforementioned memory 102. In this illustrative example, this memory has stored therein a fluence map that corresponds to the patient. Those skilled in the art will understand that fluence represents radiative flux integrated over time and comprises a fundamental metric in dosimetry (i.e., the measurement and calculation of an absorbed dose of ionizing radiation in matter and tissue). There are various approaches in the prior art that will facilitate developing such a fluence map. As the present teachings are not overly sensitive to any particular selections in these regards, further details are not provided here for the sake of brevity.

In this illustrative example this memory also contains at least one deep learning model trained to deduce a leaf sequence for a multi-leaf collimator from a fluence map. In many application settings it will be beneficial for this memory to contain a plurality of different deep learning models that are each trained to deduce a leaf sequence for a multi-leaf collimator from a fluence map.

By one approach, the at least one deep learning model comprises a neural network model. This neural network model may be trained, by one approach and at least in part, via a supervised learning method. In a supervised learning approach, one could, for example, use current sequencing algorithms (or even a highly accurate but slow algorithm) to produce the training data. In such a case, the input for the deep learning model can comprise fluence maps for each field/control point, such that a neural network model may be trained using a training corpus that includes fluence maps for each of a plurality of corresponding field/control points that correspond to the radiation treatment platform. The output, in turn, could comprise weights for a set of predefined static multi-leaf collimator openings or leaf positions of a sequence over all control points. (It may be noted that the resultant model may implicitly contain or otherwise accommodate leaf movement limits if the training set is generated using valid sequences.)

As another example, by one approach the neural network model may be trained, at least in part, via a reinforcement learning method. By one approach, the reinforcement learning method can use an agent to train the model such that for a given training fluence the agent seeks to find a best leaf sequence that will produce the target fluence. The choice of sequencing algorithm that the agent employs can be similar to the supervised learning case.

By one approach, the reinforcement learning method agent is trained based on existing cases. Although the training may be beneficially repeated for each different multi-leaf collimator apparatus, the training process itself can be both straightforward and similar. These teachings will also accommodate training different reinforcement learning method agents for different treatment sites to better match individual challenges of different cases. In some application settings a reinforcement learning approach may be preferable to a supervised learning approach because the reinforcement learning method agent can be trained against a reward that comes following a delay (including, for example, a predetermined delay), thereby allowing the training to be done based on final plan quality rather than just the current target fluence information.

By one approach the reinforcement learning approach divides the task between the agent and the environment. The agent interacts iteratively with the environment by deducing a proper action based on observation. During the training, the agent receives a reward at each iteration. By maximizing the cumulative reward the reinforcement learning method agent policy for deducing the action from observation is modified. Once the agent training is adequate, the policy is no longer changed and the agent no longer needs a reward.

With the foregoing in mind, a reinforcement learning approach can provide a training environment where the plan creation optimization algorithm can be performed automatically for a representative set of cases. Once the agent is trained and validated the agent can then be used to guide the optimization process for new patient cases. Various reinforcement learning approaches can be utilized, including Q-learning, policy gradient, and actor-critic approaches.

By one approach, the deep learning model outputs relatively higher monitor unit solutions. Those skilled in the art will understand that a monitor unit (MU) is a measure of machine output (i.e., beam-on time) from a clinical accelerator for radiation therapy such as a linear accelerator. By convention, one monitor unit equals 1 cGy of absorbed dose in water under specific calibration conditions for a medical LINAC. It will be understood that this reference to "relatively higher" refers to those solutions of a plurality of candidate and/or possible solutions that have a higher corresponding monitor unit characteristic than others of those candidate/possible solutions (for example, those solutions in the upper 10%, 25%, 40%, or 50% of all solutions having higher corresponding monitor units than the remaining solutions).

By another approach, the deep leaning model outputs relatively lower monitor unit solutions. It will be understood that this reference to "relatively lower" refers to solutions that are the opposite of the foregoing relatively higher monitor unit solutions.

These teachings are highly practical and flexible in practice and will accommodate, for example, providing at least one deep learning model that outputs relatively higher monitor unit solutions and at least one other deep learning model that outputs relatively lower monitor unit solutions.

At optional block 202, the control circuit 101 selects at least a particular one of the deep learning models for use in generating a desired leaf sequence. This optional activity can be useful, for example, when the memory contains a plurality of such deep learning models. The selection criteria can be fully or partially automatic as desired and may be based upon any of a variety of appropriate criteria in a given application setting.

At block 203, the control circuit (having access to the foregoing information in the memory) iteratively optimizes a radiation treatment plan 113 to administer the therapeutic radiation to the patient by, at least in part, generating a leaf sequence as a function of the at least one deep learning model and the fluence map that corresponds to the patient. In particular, the deep learning model deduces/generates that leaf sequence from the patient map that corresponds to the patient.

Figure 3:
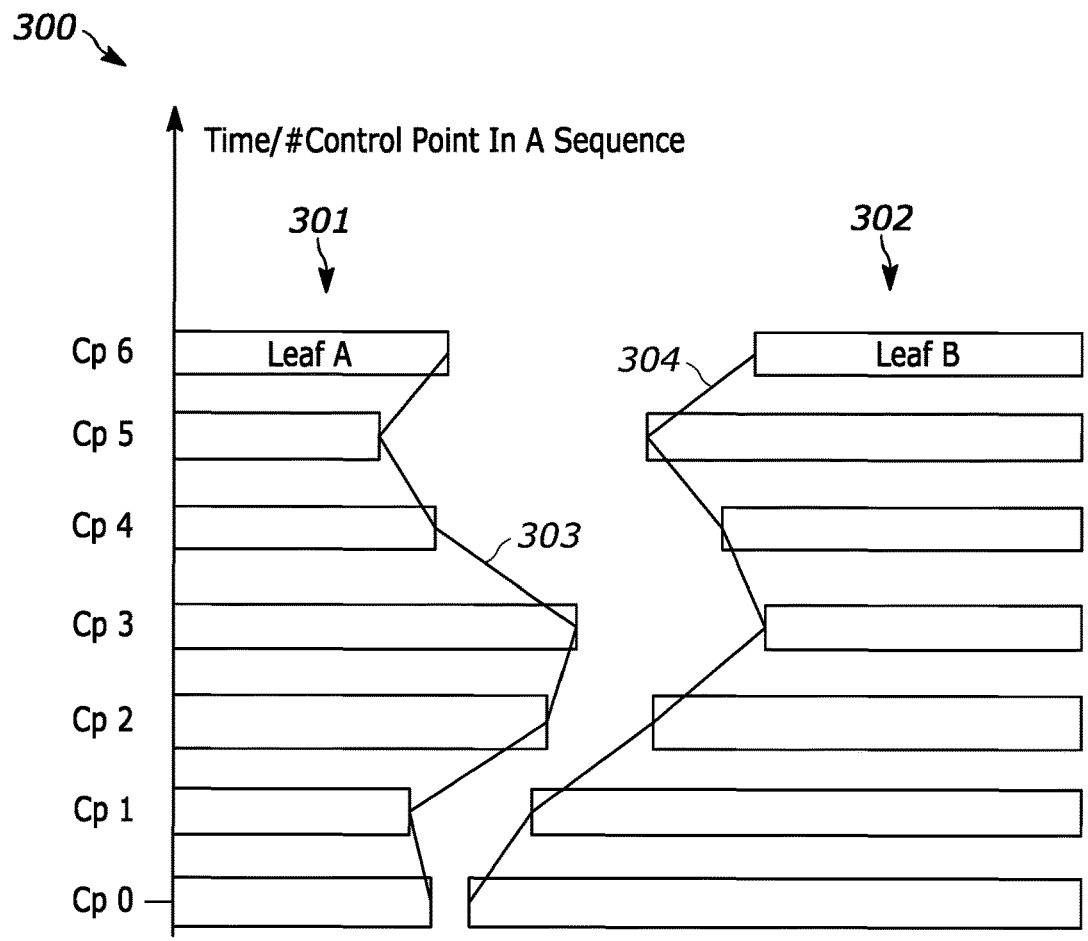
FIG. 3 comprises a schematic representation that accords with various embodiments of these teachings.

FIG. 3 presents a schematic illustration 300 that shows, on the left 301, the position of a first leaf (denoted as leaf A) and on the right 302, the position of a second leaf (denoted as leaf B) at each of a series of control points (denoted as cp 0 through co 6). A first line denoted by reference 303 serves to help illustrate the sequence of movement for leaf A and a second line 304 serves to help illustrate the sequence of movement for leaf B. Generally speaking, the deep learning approach can be taught to match certain fluence distributions with certain patterns that correspond to those sequence movement lines 303 and 304.

Figure 4:
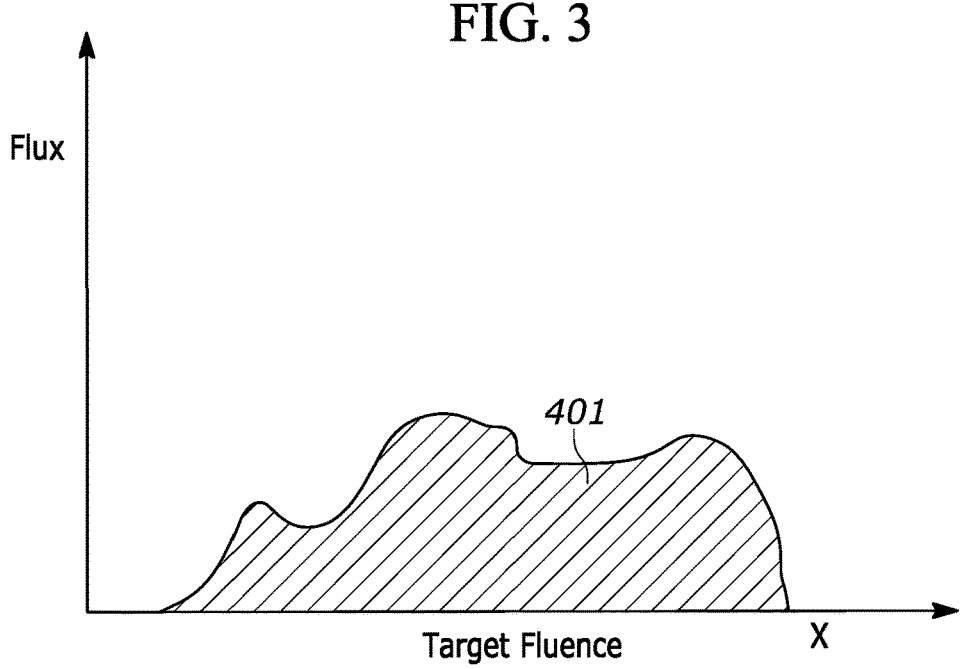
FIG. 4 comprises a graph.
Figure 5:
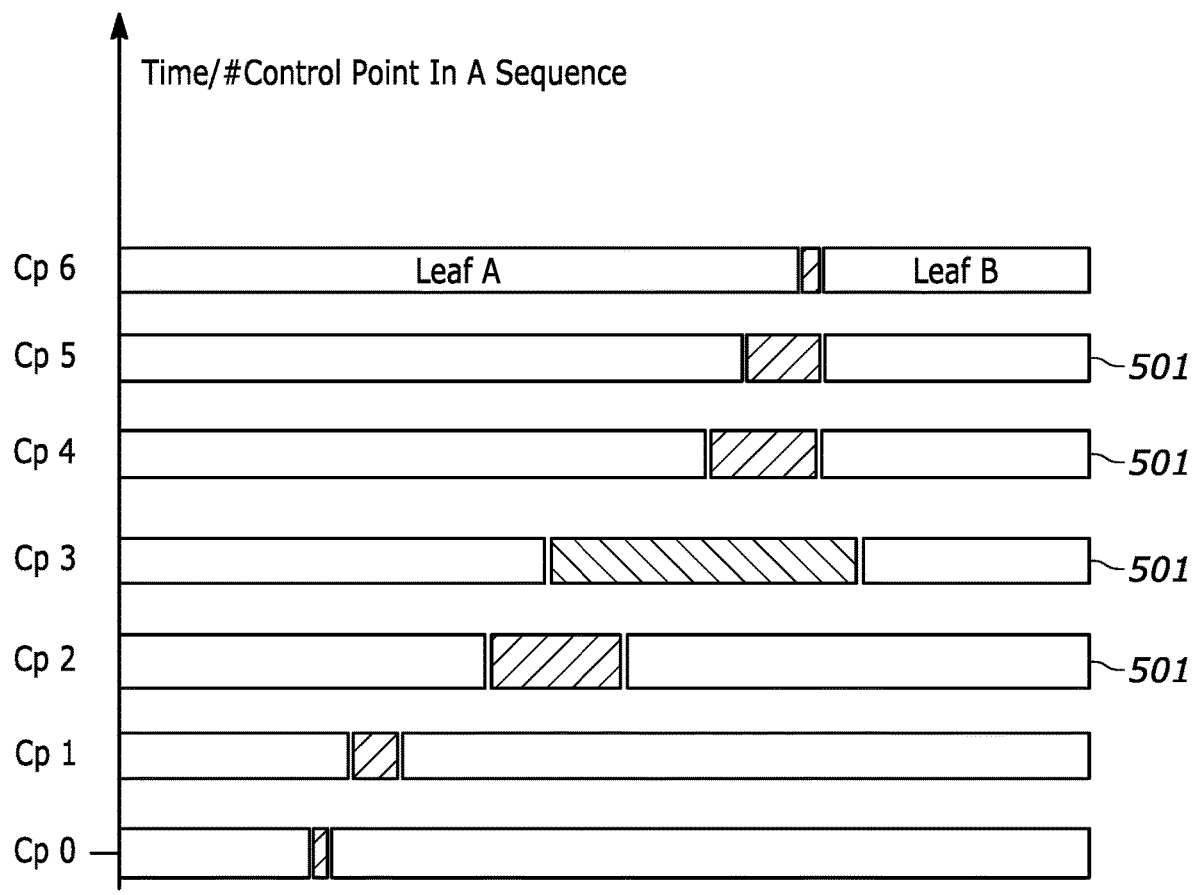
FIG. 5 comprises a schematic representation that accords with various embodiments of these teachings.
Figure 6:
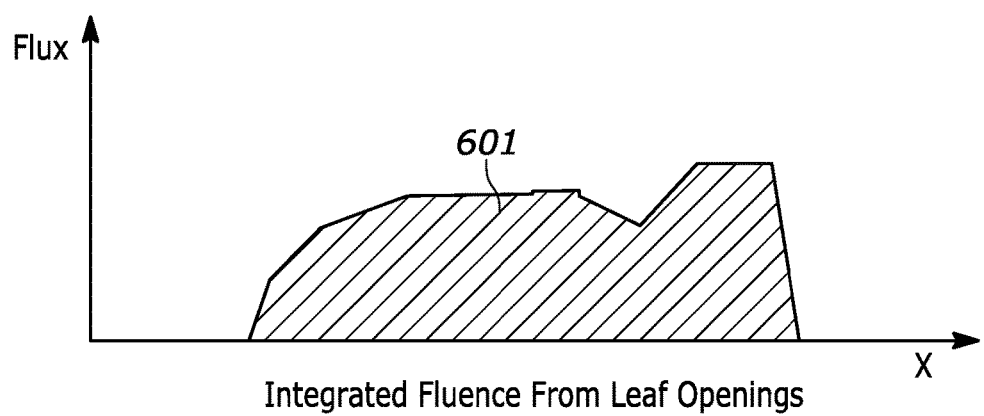
FIG. 6 comprises a graph.

FIGS. 4 through 6 present a more detailed specific example. It will be understood that this example is provided as an illustrative example and is not intended to suggest any particular limitations with respect to these teachings.

FIG. 4 presents a target fluence 401 for a particular patient. This fluence can comprise the input to the selected deep learning model(s) per these teachings.

Referring to FIG. 5, these teachings provide for finding a position X for each multi-leaf collimator leaf 501 at each control point. These approaches also determine a dose rate intensity at each control point of the sequence so that the integrated fluence will be as close as possible to the target fluence. FIG. 6 illustrates a corresponding resultant fluence 601 corresponding to the leaf openings for the determined sequence.

It may be noted that a given target fluence can be produced with multiple different control point configurations. Accordingly, one can use a given subset of all the different configurations to teach a model the desired result. As one example, such an approach can serve to create a low-monitor unit model, where the sequence lines have a simple, smooth form accompanied by a large separation between opposing leaves (it being understood that this may result in a worse match to the target fluence). As another example, such an approach can serve to create as complex a "shape" as possible (or as required) to thereby maximize the match to the target fluence (it being understood that this approach may likely produce a greater number of monitor units).

Employing a deep learning model as described to generate the leaf sequence, rather than generating such a sequence from scratch, can be faster as the actual leaf sequencing is done only during the learning phase. If desired, this process 200 will readily accommodate different models that are derived from different learning sets to accommodate different requirements for a given treatment plan. For example, a minimum monitor unit model may accommodate convex-shaped leaf apertures while another model may tolerate higher monitor units to generate highly accurate leaf sequences that reproduce the optimal fluence with maximum accuracy.

To be clear, because the inference step for a deep learning model is relatively fast, these teachings provide for speeding up the leaf sequencing part of the optimization process and also make it more adjustable to a given use case by accommodating multiple models.

The applicant has determined that the training phase may not be practical for arbitrary fluence maps as the problem size may be too large to fit in the memory and the training may take an undue amount of time. For optimization purposes the sequencing can be reduced to a one-dimensional problem if the coupling between neighboring leaves is assumed to be small (i.e., by ignoring the so-called tongue-and-groove effect). Such an assumption may be useful, for example, in VMAT optimization. Breaking that coupling reduces all possible combinations to within one fluence row. The complete fluence map could consist of multiple one-dimensional rows. Again, such an approach (i.e., one-dimensional training applied in a context with two dimensional fluence maps) may be beneficial in some application settings.

At optional block 204, therapeutic radiation is applied to the patient 104 as a function of that radiation treatment plan 113.

Those skilled in the art will recognize that a wide variety of modifications, alterations, and combinations can be made with respect to the above-described embodiments without departing from the scope of the invention, and that such modifications, alterations, and combinations are to be viewed as being within the ambit of the inventive concept.

What is claimed is:

1. An apparatus to facilitate administering therapeutic radiation to a patient, the apparatus comprising:
   a memory having stored therein:
      a fluence map corresponding to the patient;
      a plurality of deep learning models that are each trained to deduce a leaf sequence for a multi-leaf collimator from a fluence map;
   a control circuit operably coupled to the memory and configured to:
   select at least a particular one of the deep learning models;
   iteratively optimize a radiation treatment plan to administer the therapeutic radiation to the patient by, at least in part, generating a leaf sequence as a function of the at least a particular one of the deep learning models and the fluence map that corresponds to the patient.

2. The apparatus of claim 1 wherein at least one of the plurality of the deep learning models outputs relatively higher monitor unit solutions.

3. The apparatus of claim 1 wherein at least one of the plurality of the deep learning models outputs relatively lower monitor unit solutions.

4. The apparatus of claim 1 wherein a first one of the plurality of the deep learning models outputs relatively higher monitor unit solutions and a second one of the plurality of the deep learning models outputs relatively lower monitor unit solutions.

5. The apparatus of claim 1 further comprising:
   a radiation treatment platform that includes the multi-leaf collimator and that is configured to provide the therapeutic radiation to the patient as a function of the radiation treatment plan.

6. An apparatus to facilitate administering therapeutic radiation to a patient, the apparatus comprising:

a memory having stored therein:
- a fluence map corresponding to the patient;
- at least one deep learning model trained to deduce a leaf sequence for a multi-leaf collimator from a fluence map, wherein the at least one deep learning model comprises a neural network model that was trained using a training corpus that includes fluence maps for each of a plurality of corresponding field/control points;

a control circuit operably coupled to the memory and configured to iteratively optimize a radiation treatment plan to administer the therapeutic radiation to the patient by, at least in part, generating a leaf sequence as a function of the at least one deep learning model and the fluence map that corresponds to the patient.

7. The apparatus of claim 6 wherein the neural network model was trained, at least in part, via a supervised learning method.

8. The apparatus of claim 6 wherein the neural network model was trained, at least in part, via a reinforcement learning method.

9. A method to facilitate administering therapeutic radiation to a patient, the method comprising:
   accessing a memory having stored therein:
   - a fluence map corresponding to the patient; and
   - a plurality of deep learning models that are each trained to deduce a leaf sequence a multi-leaf collimator from a fluence map; and via a control circuit operably coupled to the memory:
   - selecting at least a particular one of the deep learning models
   - iteratively optimizing a radiation treatment plan to administer the therapeutic radiation to the patient by, at least in part, generating a leaf sequence as a function of the at least a particular one of the deep learning models and the fluence map that corresponds to the patient.

10. The method of claim 9 wherein at least one of the plurality of the deep learning models outputs relatively higher monitor unit solutions.

11. The method of claim 9 wherein at least one of the plurality of the deep learning models outputs relatively lower monitor unit solutions.

12. The method of claim 9 wherein a first one of the plurality of the deep learning models outputs relatively higher monitor unit solutions and a second one of the plurality of the deep learning models outputs relatively lower monitor unit solutions.

13. The method of claim 9 further comprising:
   providing the therapeutic radiation to the patient as a function of the radiation treatment plan.

14. A method to facilitate administering therapeutic radiation to a patient, the method comprising:
   accessing a memory having stored therein:
   - a fluence map corresponding to the patient; and
   - at least one deep learning model trained to deduce a leaf sequence a multi-leaf collimator from a fluence map wherein the at least one deep learning model comprises a neural network model that was trained using a training corpus that includes fluence maps for each of a plurality of corresponding field/control points; and via a control circuit operably coupled to the memory:
   - iteratively optimizing a radiation treatment plan to administer the therapeutic radiation to the patient by, at least in part, generating a leaf sequence as a function of the at least one deep learning model and the fluence map that corresponds to the patient.

15. The method of claim 14 wherein the neural network model was trained, at least in part, via a supervised learning method.

16. The method of claim 14 wherein the neural network model was trained, at least in part, via a reinforcement learning method.

* * * * *